United States Patent
Martin et al.

(10) Patent No.: US 12,334,206 B2
(45) Date of Patent: *Jun. 17, 2025

(54) FITNESS WATCH CONFIGURED WITH MICRO AI

(71) Applicants: Todd Martin, Aubrey, TX (US); Ping Zhang, Helensvale (AU)

(72) Inventors: Todd Martin, Aubrey, TX (US); Ping Zhang, Helensvale (AU)

(73) Assignee: Todd Martin, Aubrey, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/545,241

(22) Filed: Dec. 19, 2023

(65) Prior Publication Data

US 2024/0120064 A1     Apr. 11, 2024

Related U.S. Application Data

(63) Continuation of application No. 16/863,285, filed on Apr. 30, 2020, now Pat. No. 11,948,672.
(Continued)

(51) Int. Cl.
*G16H 20/30* (2018.01)
*G06N 3/08* (2023.01)
*G16H 40/63* (2018.01)

(52) U.S. Cl.
CPC ........... *G16H 20/30* (2018.01); *G06N 3/08* (2013.01); *G16H 40/63* (2018.01)

(58) Field of Classification Search
CPC . A61B 5/02438; A61B 5/02416; A61B 5/681; A61B 5/02405; A61B 2562/0219; A61B 5/0205; A61B 5/6824; A61B 5/6831; A61B 5/7246; A61B 2562/0204; A61B 5/1118; A61B 5/14542; A61B 2505/09; A61B 2562/0214; A61B 5/067;
(Continued)

(56) References Cited

U.S. PATENT DOCUMENTS

| | | |
|---|---|---|
| 10,300,334 B1 | 5/2019 | Chuang |
| 2003/0033032 A1 | 2/2003 | Lind |

(Continued)

FOREIGN PATENT DOCUMENTS

| | | |
|---|---|---|
| JP | 1994328871 | 11/1994 |
| JP | 1996215254 | 2/1996 |

(Continued)

OTHER PUBLICATIONS

Cheng JC, Chiu CY, Su TJ. "Training and Evaluation of Human Cardiorespiratory Endurance Based on a Fuzzy Algorithm." Int J Environ Res Public Health. Jul. 5, 2019; 16(13):2390. doi: 10.3390/ijerph16132390. PMID: 31284468; PMCID: PMC6651740 (Year: 2019).*

(Continued)

*Primary Examiner* — Rachel L. Porter
(74) *Attorney, Agent, or Firm* — Todd Martin (57) ABSTRACT

A system and method for biologically monitoring the fitness of an athlete, and providing a warning when an overtraining condition is determined in order to reduce injury. Through implementation of an efficient system architecture, micro-artificial intelligence use is practical for mobile situations where internet coverage is deficient or non-existent.

17 Claims, 3 Drawing Sheets

Related U.S. Application Data (60) Provisional application No. 62/982,660, filed on Feb. 27, 2020.

(58) Field of Classification Search
CPC ..... A61B 5/068; A61B 5/1123; A61B 5/4866; A61B 5/6826; A61B 5/7264; A61B 5/0002; A61B 5/02427; A61B 5/024; A61B 5/02108; A61B 5/7207; A61B 5/0059; A61B 5/0255; A61B 5/1102; A61B 5/14551; A61B 5/14552; A61B 5/6891; A61B 5/6892; A61B 5/7239; A61B 5/7455; A61B 5/0245; A61B 5/6804; A61B 5/6823; A61B 5/6833; A61B 5/7203; A61B 5/721; A61B 5/7225; A61B 5/725; A61B 5/746; A61B 2560/0406; A61B 2560/0443; A61B 2562/0233; A61B 2562/04; A61B 2562/046; A61B 5/00; A61B 5/0053; A61B 5/02055; A61B 5/0261; A61B 5/318; A61B 5/6802; A61B 5/6803; A61B 5/6815; A61B 5/6817; A61B 5/6822; A61B 5/683; A61B 5/6843; A61B 5/6898; A61B 5/70; A61B 5/7214; A61B 5/7221; A61B 5/7275; A61B 5/7282; A61B 5/7405; A61B 5/742; A61B 2503/22; A61B 2560/0214; A61B 2560/0468; A61B 2562/0247; A61B 2562/0257; A61B 2562/0271; A61B 2562/029; A61B 2562/06; A61B 5/0022; A61B 5/0077; A61B 5/01; A61B 5/02; A61B 5/021; A61B 5/02125; A61B 5/02152; A61B 5/0225; A61B 5/02433; A61B 5/02444; A61B 5/029; A61B 5/08; A61B 5/082; A61B 5/1072; A61B 5/11; A61B 5/1116; A61B 5/222; A61B 5/24; A61B 5/28; A61B 5/316; A61B 5/332; A61B 5/352; A61B 5/369; A61B 5/389; A61B 5/4088; A61B 5/4227; A61B 5/441; A61B 5/6805; A61B 5/72; A61B 5/7235; A61B 5/7253; A61B 5/7257; A61B 5/7267; A61B 5/7445; A61B 7/003
See application file for complete search history.

(56) References Cited

U.S. PATENT DOCUMENTS

| | | | |
|---|---|---|---|
| 2008/0077620 A1 | 3/2008 | Gilly | |
| 2009/0069156 A1 | 3/2009 | Kurunmaki | |
| 2010/0131291 A1 | 5/2010 | Firminger | |
| 2010/0174205 A1 | 7/2010 | Wegerif | |
| 2014/0035745 A1 | 2/2014 | Bell | |
| 2014/0275852 A1 | 9/2014 | Hong | |
| 2016/0066820 A1 | 3/2016 | Sales | |
| 2016/0196758 A1* | 7/2016 | Causevic | A61B 5/165 434/236 |
| 2016/0361020 A1 | 12/2016 | LeBoeuf | |
| 2016/0374569 A1* | 12/2016 | Breslow | A63B 24/0087 600/301 |
| 2017/0120107 A1* | 5/2017 | Wisbey | A61B 5/1118 |
| 2017/0188668 A1 | 7/2017 | Watterson | |
| 2017/0209055 A1* | 7/2017 | Pantelopoulos | A61B 5/02108 |
| 2018/0109589 A1 | 4/2018 | Ozaki | |
| 2019/0278895 A1 | 9/2019 | Streit | |
| 2019/0336824 A1* | 11/2019 | Fung | A63B 22/0285 |
| 2020/0038730 A1 | 2/2020 | Khan | |
| 2020/0175886 A1 | 6/2020 | Jain | |
| 2020/0261023 A1* | 8/2020 | Werbin | A61B 5/01 |
| 2023/0307124 A1* | 9/2023 | Sanders | A41D 1/002 |

FOREIGN PATENT DOCUMENTS

| | | | | |
|---|---|---|---|---|
| WO | WO-2018049531 A1 * | 3/2018 | ........... | A61B 5/0205 |
| WO | WO-2019165000 A1 * | 8/2019 | ........... | G06F 16/288 |
| WO | 2021007581 | 1/2021 | | |
| WO | WO-2021007581 A1 * | 1/2021 | ......... | A61B 5/02405 |

OTHER PUBLICATIONS

Sarker, Iqbal, "Machine Learning: Algorithms, Real-World Applications and Research Directions," SN Computer Science (2021) 2:160 (Published Online: Mar. 22, 2021).

Top 10 Artificial Intelligence Problems, CloudMoyo, (<www.cloudmoyo.com/blog/ai-ml-automation/top-10-potential-ai-artificial-intelligence-problems/> (2021)(author not listed).

Maayan, Gilad, "Supercomputers and Machine Learning: A Perfect Match," insideBIGDATA (Nov. 27, 2019).

Torres, Jordi, "Artificial Intelligence is a Supercomputing problem, Supercomputing For Artificial Intelligence"—01 (Nov. 12, 2020).

Cheng, JC, CY, Su TJ. "Training and Evaluation of Human Cardiorespiratory Endurance Based on a Fuzzy Algorithm," Int J Environ Res Public Health, Jul. 5, 2019; 16(13):2390, doi 10.3390/ijerph16132390, PMID: 31284468: PMCID: PMC6651740 (Year: 2019).

International Search Report for PCT/US21/19729 (May 20, 2021)(3 pages).

Written Opinion of the International Searching Authority for PCT/US21/19729 (May 20, 2021)(5 pages).

Supplementary European Search Report for related European Application No. 2175935 dated Feb. 23, 2024.

\* cited by examiner

FITNESS WATCH CONFIGURED WITH MICRO AI

This application is a continuation of U.S. application Ser. No. 16/863,285, filed Apr. 30, 2020, which claims the benefit of U.S. Provisional Patent Application No. 62/982,660, filed Feb. 27, 2020, the entire contents of each of which is hereby incorporated by reference herein.

FIELD OF THE INVENTION

The present disclosure relates to improvements in systems and methods for physically identifying biological conditions where overtraining and injury will cause an alteration in fitness training activities, and the architecture and design of a system configured to reduce memory storage requirements for certain intelligence-based applications on a mobile device.

BACKGROUND OF THE INVENTION

Some athletes choose a goal competition (e.g., New York City Marathon), and attempt to implement a training program with little consideration as to a likelihood of injury. The athlete becomes extremely focused, and often misses cues, or simply is unaware or unable to determine signs of overtraining and the approach of an injury condition. It would be helpful for the athlete to be able to receive an overtraining indication from a device they carry with them on a training activity, such as a fitness tracker or similar device.

Artificial intelligence ("AI") and machine learning algorithms are becoming more cemented in today's society to solve a number of problems. Conventional AI techniques utilise large data sets in order to identify patterns and draw conclusions. Conventional AI techniques are simply ill-suited for use in mobile devices of the type likely to be carried by an athlete for a variety of reasons. First, the typical memory requirement needed to accommodate large data sets ordinarily used by conventional AI would be quite large. Secondly, the processing capability needed to generate conclusions obtainable from conventional AI techniques is likewise large. Thirdly, when an athlete trains, typically they venture into areas where there is not a Wi-Fi network, and hence no internet. Where the athlete's device has provision for cellular coverage, there are still areas where cellular coverage is non-existent, or compromised. Even where cellular coverage is available, the cost of large data transmissions would make use of such cellular coverage for typical AI methodology cost-prohibitive and not pragmatic. What is needed is a system and method that encapsulates the ability to provide an analysis and warning or indication of an elevated overtraining condition so that modifications to a training program can be made before it is too late, and an overtraining or injury situation arises.

SUMMARY

The present disclosure in one aspect provides for a less complicated system and method of providing an athlete/user with identification and advanced warning of an overtraining condition. In instances utilizing artificial intelligence ("AI"), the system and methodology provides for a configuration which reduces memory requirements, communications, and processing requirements to permit "micro-AI" to become a reality. In one aspect, the system and method utilize bifurcated data organized into "latent data" and "current data". Latent data is further preferably organized into general historical athlete data (which may be categorical across a range of non-particular individuals), and historical data particular to the individual athlete. The scope of data useable by micro-AI is reduced and organized for efficiency compared to traditional AI systems, which permits mobile applications in a realistic manner.

The present disclosure in another aspect sets forth a method of generating a set of latent features relating to historical training patterns and outcomes; periodically refreshing a wearable fitness device worn by the athlete with the latent features; recording current training data of the athlete as the athlete is training to generate a set of current features, the current features including a heart rate; performing a statistical application with the latent features and the current features to generate a feature vector indicative of an overtraining condition; feeding the feature vector into a neural network or any other classifier selected residing on the wearable fitness device; and obtaining a result from the neural network as to whether an overtraining condition is present.

It will be appreciated that references herein to "training" includes exercise in general, and that a person partaking in training activities need not be a professional athlete, but anyone with an interest in exercising.

As used herein, "configured" includes creating, changing, or modifying a program on a microprocessor, computer or network of computers so that the processor, computer or network of computers behave according to a set of instructions. The programming to accomplish the various embodiments described herein will be apparent to a person of ordinary skill in the art after reviewing the present specification, and for simplicity, is not detailed herein. The programming may be stored on a computer readable medium, such as, but not limited to, a non-transitory computer readable storage medium. The system may be implemented on a field-programmable gate array and graphics processing unit.

It is to be understood that both the foregoing general description and the following detailed description are exemplary and explanatory only and are not restrictive of the invention, as claimed, unless otherwise stated. In the present specification and claims, the word "comprising" and its derivatives including "comprises" and "comprise" include each of the stated integers, but does not exclude the inclusion of one or more further integers. The claims as filed with this application are hereby incorporated by reference in the description. The entire disclosures of U.S. Pat. Nos. 10,124,234; and 10,322,314 are hereby incorporated by reference herein.

The accompanying drawings, which are incorporated in and constitute a part of this specification, illustrate several embodiments of the invention and together with the description, serve to explain the principles of one or more forms of the invention.

DETAILED DESCRIPTION OF THE DRAWINGS

Reference will now be made in detail to exemplary embodiments of the invention, some of which are illustrated in the accompanying drawings.

Figure 1:
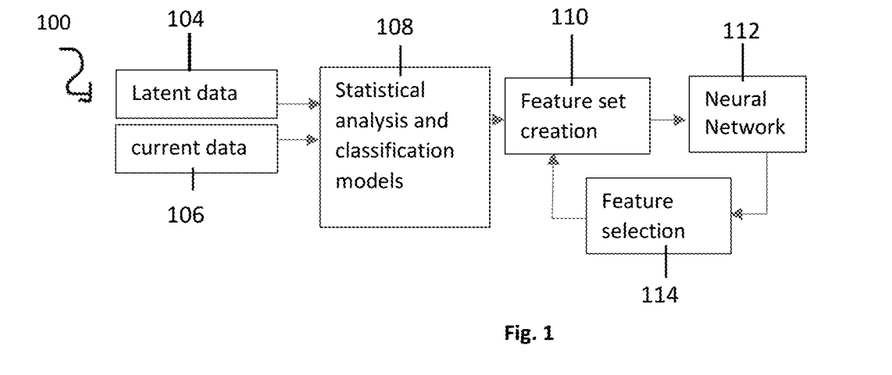
FIG. 1 is a flow diagram of a method for determining an overtraining condition in accordance with an embodiment of the disclosure.

FIG. 1 shows a flow diagram of a method and system 100 of providing an athlete with identification and advanced warning of an overtraining condition, or a condition where certain training is not suitable. An exemplary situation where training might not be suitable is where the athlete has asthma, and weather conditions are not conducive to the athlete's condition. It will be appreciated that although a preferred embodiment is described in relation to overtraining conditions, the disclosure has broader applications as will be further described below. In brief, in a fitness device 124 (FIG. 2) carried by an athlete, the device 124 is configured with bifurcated data organised into "latent data" 104 and "current data" 106. Latent data 104 is preferably further organised into general historical athlete data (which may be categorical across a range of non-particular individuals), and specific historical data particular to the individual athlete. Latent data is updatable at convenient opportunities, such as when the device enters a known Wi-Fi network. Current data 106 is updated as the user trains during a training activity, irrespective of internet coverage, and can be later uploaded automatically to a remote server to update any latent data stored on the remote server when Wi-Fi is available (or via any internet connection as set up). Using pre-defined parameters, a fitness device with an onboard processor with micro-artificial intelligence capabilities utilizes a combination of the data groupings to feed an onboard neural network and other classifiers, depending upon the intended use, to identify the existence of an overtraining condition and provide a warning to the athlete that the overtraining condition exists, and provide alternatives for altering a training plan to avert a potential overtraining situation and injury. The scope and quantity of data useable by micro-AI is reduced compared to traditional AI systems, which permits mobile applications in a realistic manner.

As described already, latent data 104 may include general historical athlete data, and specific historical data particular or personal to the individual athlete. General historical data is that which pertains, for example, to demographical data in a general human population, and may be categorized and sub-categorized. For example, if an athlete is a 40 year-old male runner, general historical data would focus on a subset of the human population directed to male runners in the 40-44 year-old age group. Other factors could take into account geographical location, exercise type (e.g., running, and whether marathoner or sprinter), demographical data (age, gender), experience in a particular activity (e.g., new to the activity, or years of experience in the activity), terrain (e.g., hilly, flat), and climate (e.g., hot, cold, humid).

Specific historical data is that which pertains to the athlete's own personal characteristics and experience. For example, such data items may include an injury prone factor (a person's susceptibility to being injured, or how durable they are from heavy exercise), family history/genetics, specific experience in the activity, and a training goal (fitness level or upcoming competition). For training organization, the athlete's goal, and time (e.g., time between exercise sessions, sleep time, and time remaining to a goal competition, such as how many days or weeks remaining to the competition date) may be accommodated.

Other indicators and factors pointing to an overtraining condition include measuring and recording a fatigue factor (a subjective factor as to how tired someone feels), muscle soreness, a sweat index (how much the athlete is sweating, preferably taking into account humidity level), and VO2 max data (maximal oxygen uptake, which relates to the maximum amount of oxygen that a person can utilize during intense exercise). The VO2 max data is usually obtained by testing with an athlete on a treadmill in combination with a breath mask. As may be seen, features can be all objective, subjective, or a combination of objectively and subjectively derived features.

Current data 106 is data which is updated and stored on the athlete's fitness device, such as fitness device 124 (FIG. 2) as the athlete is training, and tracks aspects of the athlete's training activity such as exercise type (e.g., core work, yoga, swimming, cycling, running), exercise duration (accumulated time, and time of different segments of the exercise), exercise location (geography), elevation changes, and heart rate. Such data is stored for a predetermined length of time, for example, two weeks, after which such data is automatically deleted as "expired" current data from the fitness device. Storage of current data for a predetermined time preserves memory for more current data. Other time periods can be accommodated, for example only, days, or even hours depending upon the intended use. Meanwhile, current data can be uploaded automatically or manually from device 124 to a remote server when the device is in an internet coverage area to be merged or integrated with the latent data residing on the remote server, as set forth in more detail below.

Figure 2:
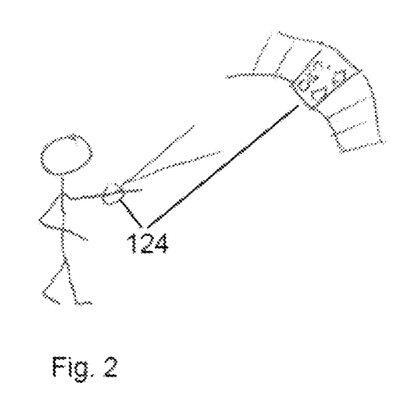
FIG. 2 is a pictorial view of an athlete wearing a fitness tracking device.

Referring to FIG. 2, device 124 may be a Global Positioning System (GPS) fitness tracker with processing and memory configured to log athlete training data. Device 124 may be a body-worn device, for example, a fitness tracker worn about a user's wrist, chest or head. For example, device 124 may be incorporated as a part of a wristwatch, swim goggles, a cycle helmet, a chest strap, or even running shoes. Device 124 may include a Wi-Fi radio transceiver and/or a Bluetooth radio transceiver. Device 124 may be paired with a mobile communications device such as a smartphone to utilize a smartphone's memory capability. Some exercise types do not lend themselves to permitting a smartphone to be carried by the athlete while the athlete is training, for example, swimming.

The timeframe for automatic deletion of current data may be based on the volume of current data. For example, 14 days of training data may be stored, regardless of the actual date of when the training occurred. That way, if it has been a week since the device was last used, there will still be two weeks' worth of current data on the device.

The system may be configured so that the current data is merged or integrated with the latent data residing on the remote server when internet is available to update the latent data. For example, when the latent data is refreshed once device 124 is in an internet coverage area, portions of the current data may be added to the latent data, for example, the athlete's specific historical data is updated with recent activities from the current data. The refreshing of the latent data (e.g., of the athlete's specific historical data with elements of the current data) may be based on the expired current data (data older than the predetermined time frame), and/or based on all of the athlete's training data (specific historical and current as of the most recent training activity). If desired, only the expired current data may be used to update the latent data so that a merger of expired current data and latent data is completed at the remote server, using archived current data where such current data was archived. In the event of utilization of archived data, a decompressor may be used prior to the merger/integration of data.

In a preferred embodiment, latent data is not constantly updated or refreshed with the current data, but maintained separately as a different component of the device memory. Therefore, for example, during training sessions, the amount of latent data remains substantially unaltered.

Heart rate data may be of two general types, active heart rate (the heart rate during training), and at-rest heart rate (e.g., a heart rate measured when an athlete first awakes at the start of the day). Active heart rate can be weighted or analysed against historical heart rate data (general category and/or specific individual).

An at rest heart rate, or a "waking heart rate" (WHR) is a very good indicator of fitness and overtraining. Usually taken when someone wakes up, a pulse of upper 30 s beats per minute usually means that person is fit. Even a pulse in the 40 s is a sign of good fitness. A waking heart rate may be measured by a fitness device having a heart rate sensor if the fitness device is worn to bed by the athlete, or may be manually derived from the athlete taking their pulse in a prone position.

A real time "active heart rate" monitoring (typically with a fitness tracking device), during exercise can also indicate fitness and overtraining, but is usually tied to physical exertion and effort. Usually, a heart rate of 60 to 90 beats per minute means someone is at a low activity (e.g., walking or sitting). A range of between 100-140 is usually an indicator of moderate activity. A range of around 140 to 160 is an indicator of harder activity. A heart rate of between 170 to 200 typically indicates peak exertion. A maximum heart rate depends on age. Younger people (in their 20 s and 30 s) should be able to have a max heart rate of around 200. The max heart rate has been shown to decrease with age. For someone in their 40 s, the max heart rate might be 190.

Preferably, a set of 17 features relating to overtraining conditions, including 9 latent features (e.g., age, heart rate, age difference from the average age within a particular sport, exercise duration, exercise amount, past injuries, past intensity measurements, variables derived from statistical analysis based on historical data, parameters from statistical tests or regressions) and 8 current features (e.g., heart rate (active and at rest), exercise duration, exercise type, time between exercise sessions, exercise amount, intensity level, sleep time) are utilized for classification.

Intensity level may be measured by a combination of heart rate, or heart rate and pace (speed) when the exercise involves travel over a distance, or weight amount for weight training.

It will be appreciated that varying combinations of features may be used without departing from the scope of this disclosure. For example, more or less than 9 latent features may be utilized. More or less than 8 current features may be utilized. The feature set may include any feature that contributes to identification of an overtraining condition. A few more important features in relation to detecting overtraining conditions include heart rate, training duration, and intensity (depending upon the form of exercise), in combination with historical and demographical data.

Referring to FIG. 1, once a set of features has been generated, the set is preferably classified using one or more classifier models 108 to create second order features. Referring to FIG. 1, a NN classifier 112 is used to distinguish between normal training and abnormal training, taking into account normal population, and specific characteristics of an individual. There are a variety of techniques suitable for use as a classifier. Suitable classifiers include, but are not limited to statistical applications (e.g., Bayesian, K-nearest neighbour, fuzzy pyramid linking, discriminant analysis (DA), logistic regression (LR), multivariant adaptive regression splines (MARS), support vector machine (SVM), and Hidden Markov Model), neural networks (parallel, double, deep learning recurrent), decision trees, associated rule mining, and case-based reasoning, or a combination of any of the foregoing.

A neural network ("NN") typically involves an artificial neuron, where a set of inputs is applied, each representing an output of another neuron. Each input is multiplied by a corresponding weight which is analogous to synaptic strengths in biological neurons. The weighted inputs are summed to determine the net input of the neuron. This net input is processed further by using a squashing function (activation function), to produce the neuron's output signal. This function may be linear, nonlinear (e.g. step function) or sigmoid (S shaped).

Examples of weighted inputs include heart rate being a given a higher weighting, while exercise duration, short term sleep (e.g., in the last 24 hours), and waking heart rate being given a lower weighting.

Referring again to FIG. 1, for NN application 112, the current features extracted from the current data 106 and second order features from classifier models 108 are preferably normalized to create a feature set 110 to improve the training efficiency. All the features are preferably normalized as the real numbers in the range of 0 to 1 based on the whole dataset used for training and testing.

A feature vector is preferably created for every condition associated with overtraining, and with the current features 106 plus the outputs from one or more classifier models 108 (e.g., the LR, DA and MARS models). In this step a file with vectors including, for example, 20 features for all the cases is created.

The features are preferably normalized before the feature file can be efficiently used by NN 112. The normalized combined feature-vectors are fed into the neural network 112 for further classification.

It will be appreciated that ways other than statistical applications may be used to provide further features, or second order features. For example, data mining techniques or other classifiers such as neural networks, decision trees, associated rule mining, and case-based reasoning, or a combination of any of the foregoing, may be used to provide second order features which may be eventually fed into a neural network.

Other applications may be used in place of, or in addition to the NN as a final classifier. For example, the NN may be used in combination with SVM, or substituted by SVM for final classification if desired.

If desired, a micro-AI analysis can be conducted in a real-time exercise situation, i.e., as the athlete is training. A micro-AI analysis during training consumes more device power and processing capabilities, but can be conducted if conditions are warranted (e.g., if a condition exists to trigger local during-training AI analysis). Several levels of triggers may be utilized. For example, a primary trigger may be active heart rate level. Heart rate is one of the most important metrics in ascertaining the existence of overtraining conditions. Second degree triggers may include one or more of training duration, short term sleep (e.g., sleep over the last 24 hours), training intensity, and WHR. Real-time micro-AI analysis may be initiated solely by a primary trigger (e.g., a heart rate going beyond a predetermined threshold), or a combination of secondary triggers (e.g., a combination of current training duration being greater than a threshold level, sleep level being less than a predetermined minimum, and a WHR above a predetermined threshold), or a combination of primary and secondary triggers (e.g., active HR in combination with a training intensity). When using active heart rate, the micro-AI analysis compares the current data of the active heart rate and training intensity level (in a running situation, running pace) with latent data pertaining to specific historical data of the individual (active heart rate and intensity level) to determine if the active heart rate is beyond a predetermined threshold, indicating an overtraining condition is present that could lead to an injury condition.

Once real-time micro-AI is triggered, the micro-AI analysis is conducted while the athlete is training. If the result is that an overtraining condition exists while the athlete is training, a warning is provided to the athlete while they are training. Such warning can be provided through fitness device 124 where it is configured to provide one or more of an audible signal, a vibratory indication, and/or visual warning. The warning may be provided through the use of a paired smartphone should the smartphone be within range.

Referring again to FIG. 2, fitness monitoring device 124 preferably includes a heart rate sensor, and an onboard memory that includes a latent memory component configured to retain latent data including non-individual data not particularly pertaining to the user, and including personal data particular to the user. The latent memory is preferably updatable only when the tracker is within an internet coverage area. One result of this is that the amount and type of data in the latent memory is finite compared to cloud servers, reducing the quantity of data that is otherwise analyzed as part of any AI analysis when confining an AI analysis to only data in the device onboard memory.

The memory of device 124 further includes a current memory component configured to retain current data that is updatable as the user is training. Device 124 also includes a processor, such as a microprocessor, that includes a classifier. The processor is configured to determine an existence of an overtraining condition, and other determinations as needed, based on a prediction model utilizing data only in the device onboard memory irrespective of presence in an internet coverage area. The processor is configured to provide an alert to the user after determining that the overtraining condition exists according to an output of the classifier. In a preferred embodiment, the processor is configured to compare the current data with the latent data and determine an existence of an overtraining condition.

Figure 3:
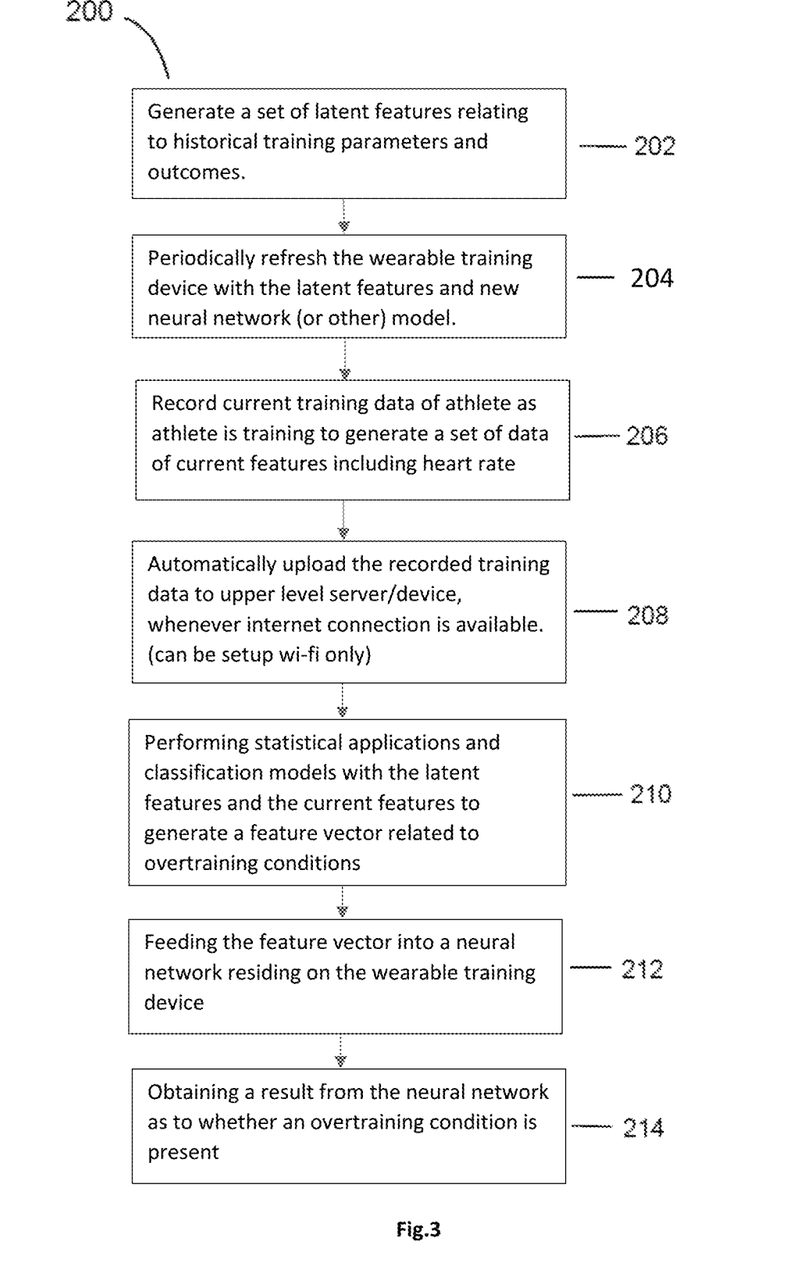
FIG. 3 is a flow diagram of a method for classifying an overtraining condition for use in a neural network.

Having described the preferred components of system 100, a preferred method 200 for classifying an overtraining condition of an athlete is shown in FIG. 3. The method includes in step 202 generating a set of latent features relating to historical training patterns and outcomes; in step 204, periodically refreshing a wearable fitness device worn by the athlete with the latent features; in step 206, recording current training data of the athlete as the athlete is training to generate a set of current features, the current features including a heart rate; in step 208, automatically uploading recorded training data to a server when the device is in an internet coverage area to update any latent features stored on the server; in step 210, performing, with the onboard processor of the wearable fitness device, a statistical application and one or more classifier models with the latent features and the current features in the device memory to generate a feature vector for predicting the overtraining condition; in step 212, feeding the feature vector into a neural network residing on the wearable fitness device, that was created based on the selected features; and in step 214, obtaining a result from the neural network as to whether an overtraining condition is present. The method may include the step of the wearable fitness device being refreshed only when the device is in an internet coverage area. The method may include refreshing the latent data, for example, the specific historical data of the athlete, with expired and/or non-expired current data at a remote server. The method may also include the step of the result being obtained from the neural network based only on data stored in the wearable fitness device.

It will be appreciated that the steps described above may be performed in a different order, varied, or some steps added or omitted entirely without departing from the scope of the disclosure. For example, the method may include monitoring an athlete's heart rate during training and comparing the active heart rate with a historical intensity level, depending on the form of exercise. If the heart rate is above a threshold value, preferably taking into consideration one or more of intensity, speed, and duration, then an AI analysis is triggered to determine whether the elevated heart rate may represent an overtraining condition and indicate the approach of an injury condition while the athlete is training. If the analysis determines an overtraining condition is present, then the method may including sending an alert to the athlete, preferably using the wearable fitness device. The alert may be delivered as an auditory message, a vibratory indication, and/or a visual indication. The alert may specify that the athlete decrease training intensity, slow down, walk, or stop to reduce injury risk. If the analysis determines that an overtraining condition is not present, then the athlete's heart rate is continued to be monitored.

Practical Example 1

Let's say Joe Smith is a 40-year-old runner who has been running for 3 years. He lives in the Gold Coast hinterland of Australia (hilly area in a warmish climate). His dad was a professional runner. His mother was an average rower. Joe's goal is to run the Gold Coast Marathon in 3 months.

Latent Historical Data (General) Historical patterns for male 40-44 years old show that 40-50 Kilometers a week lead to a decent health fitness (e.g., average wake up heart rate (WHR) of 45 beats per minute).

(Specific) Joe's own historical data is based on his last 3 years. He averaged 40K per week, maintaining decent health (average wake up HR 50), but became injured one time when he ran 80K per week.

Current Data

Joe's training data is stored automatically on his fitness tracking device for up to 2 weeks every time he exercises. This includes his heart rate (active and wake-up). On a given day, Joe logged in a long 15K run to prepare for the marathon. This is one day after he ran 20K. He only slept 4 hours. His wake-up HR was only 62.

Conclusions: Joe's wake up HR is elevated compared to his personal "fit" HR, and deviates from the general athlete population of 40-year-old men "fit" HR too. The other factor is the two days in a row of longer than normal training. The HR combined with the duration of exercise suggests that Joe is over-training. Joe complained of sore muscles (sharp pain) after his second day 15K run. Joe has historically been injured when he has done too much without sufficient recovery between long or hard sessions. Based on the latent historical data (general and specific), and the current data (HR), the resulting conclusion from the micro-AI on Joe's device is that Joe is overtraining and needs to alter his training regimen. This conclusion is based on the technical conclusion further described below. The sharp pain is a flag that he is at high risk of injury, and needs to significantly alter his training by taking a day or two off.

Technical conclusion: an overtraining conclusion is derived from latent historical parameters using statistical applications stored on the fitness tracker, combined with current data on the fitness tracker. Current data HR, intensity, and training duration (time and/or distance), combined with analysis that compares historical individual trends and historical general population category trends is utilized.

Output: an analysis which shows that training is on track towards a goal (can be visually presented per a curve), or that training needs to be altered due to overtraining and/or elevated injury risk. This may be delivered as a warning on the fitness tracker (verbal, vibratory, and/or visual), or via another connected device.

Practical Example 2

Following on from the above example, Joe decides to go on a 10K run the day after his 15K run. His WHR is 65, and he had 7 hours of sleep. Feeling tired, he decides to go for an easy run. Ten minutes into the run, his active heart rate reaches 180 beats per minute as measured by the heart rate sensor on the fitness tracker worn by Joe. The micro-AI component of Joe's fitness tracker analyses Joe's current active heart rate and intensity level compared to latent specific historical data and determines that the heart rate is overly elevated given Joe's relaxed pace, activating the primary trigger. The processor on Joe's fitness tracker sends an audio, vibratory and visual warning to Joe alerting him that he ought to cease further training or risk becoming injured.

The system may be configured for use with activities other than athletic activities such as running, cycling, swimming or multisport. For example only, the system may be configured for use with forms of exercise such as kayaking, crew, hiking, yoga, weight training, core sessions, and other sports or athletic activities.

Other sensors may be used in combination with a heart rate sensor, or in instead of a heart rate sensor to help ascertain an overtraining condition and to minimize injury risk. For example, one or more movement sensors may be used to determine proper running gait, cycle form or swim stroke analysis to increase training efficiency and lower injury risk.

Information or data normally stored at a remote physical location may be stored in the Cloud, considerably reducing the onsite hardware needed for memory requirements often associated with large volumes of data.

The features described with respect to one embodiment may be applied to other embodiments, or combined with or interchanged with the features of other embodiments, as appropriate, without departing from the scope of the disclosure.

The present disclosure in one or more preferred forms provides the advantages of being more responsive, more convenient, involving reduced data transmission (saves on communication resources), and being capable of being used even when out of communications range, which can happen on training segments. Lessor memory is required since lesser bulk data is being stored for constant analysis.

Other embodiments of the disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A fitness watch, comprising:
   a heart rate sensor configured to provide heart rate data of the user;
   a bifurcated memory structured to reduce a quantity of data subject to an artificial intelligence analysis, said bifurcated memory including:
   a latent memory configured to retain latent data including demographic; and historical, non-current exercise data, said latent memory being periodically updatable defined by when the fitness watch is within an internet coverage area;
   a current memory configured to retain current data that is updatable as the user is exercising, irrespective of internet coverage, the current data including heart rate data provided by said heart rate sensor, said latent memory and said current memory being differentially updatable relative to one another, depending upon presence of the fitness watch in the internet coverage area; and
   a microprocessor including a neural network, said microprocessor being configured to determine an existence of an overtraining condition based on an output of the neural network utilizing only updatable and periodically updatable data in said bifurcated memory to enable operation of the neural network in a mobile environment, said microprocessor being configured to provide an alert to the user after determining that the overtraining condition exists according to the output of the neural network.

2. The fitness watch of claim 1, wherein the determination is based on active heart rate of the user while the user was exercising.

3. The fitness watch of claim 1, wherein the determination is based on a combination of active heart rate and at least one of a training intensity level and training duration.

4. The fitness watch of claim 1, wherein said microprocessor is configured to compare said current data with said latent data to determine the existence of the overtraining condition.

5. The fitness watch of claim 1, wherein said neural network utilizes a Bayesian classifier to generate the output.

6. The fitness watch of claim 1, wherein said microprocessor is configured to determine the existence of an overtraining condition as the user is exercising.

7. The fitness watch of claim 1, wherein said microprocessor is configured to determine the existence of the overtraining condition based on the output of the neural network while the user is exercising.

8. The fitness watch of claim 1, wherein the determination of the existence of the overtraining condition is triggered by a weighted trigger condition.

9. The fitness watch of claim 8, wherein a primary trigger is heart rate, and a secondary trigger is sleep duration.

10. The fitness watch of claim 1, wherein said microprocessor is configured to provide the alert to the user while the user is exercising.

11. The fitness watch of claim 1, wherein the output of the neural network is based on at least two classifiers, one of the classifiers being a Bayesian classifier.

12. The fitness watch of claim 1, wherein said microprocessor is configured to generate a fitness condition based at least on a combination of active heart rate and pace.

13. The fitness watch of claim 1, wherein said microprocessor is configured to generate a fitness condition based on sleep time.

14. The fitness watch of claim 1, wherein the latent data includes geographic data.

15. The fitness watch of claim 1, further comprising a movement sensor.

16. The fitness watch of claim 1, wherein said microprocessor is configured to provide an alert cautioning the user to alter training frequency.

17. The fitness watch of claim 1, wherein said microprocessor is configured to provide an alert warning the user to alter a duration of exercise.

* * * * *